US012336851B2

(12) United States Patent
Lazarev et al.

(10) Patent No.: US 12,336,851 B2
(45) Date of Patent: Jun. 24, 2025

(54) DIFFRACTIVE ANALYZER OF PATIENT TISSUE

(71) Applicant: Arion Diagnostics, Inc., Petaluma, CA (US)

(72) Inventors: Alexander P. Lazarev, Lake Forest, CA (US); Pavel I. Lazarev, Menlo Park, CA (US); Delvin Tai Wai Yuk, Atherton, CA (US)

(73) Assignee: Arion Diagnostics, Inc., Petaluma, CA (US)

( * ) Notice: Subject to any disclaimer, the term of this patent is extended or adjusted under 35 U.S.C. 154(b) by 129 days.

(21) Appl. No.: 18/137,342

(22) Filed: Apr. 20, 2023

(65) Prior Publication Data

US 2023/0341340 A1    Oct. 26, 2023

Related U.S. Application Data

(60) Provisional application No. 63/333,079, filed on Apr. 20, 2022.

(51) Int. Cl.
*A61B 6/04*     (2006.01)
*A61B 6/00*     (2006.01)
(Continued)

(52) U.S. Cl.
CPC .............. *A61B 6/50* (2013.01); *A61B 6/0421* (2013.01); *A61B 6/4035* (2013.01);
(Continued)

(58) Field of Classification Search
None
See application file for complete search history.

(56) References Cited

U.S. PATENT DOCUMENTS 3,639,764 A * 2/1972 Olson ................. G01N 23/083
                                                    378/175
3,824,397 A * 7/1974 Bauer .................... A61B 6/502
                                                    378/180
(Continued)

FOREIGN PATENT DOCUMENTS

CN      110907483 A     3/2020
CN      109324072 B     5/2021
(Continued)

OTHER PUBLICATIONS

Goldstein, Mark R. et al., "Might tumor secreted cathepsin proteases leave specific molecular signals in skin, hair and nails years before a cancer becomes clinically apparent?" Medical Hypotheses 103, pp. 62-63 (2017).
(Continued)

*Primary Examiner* — Thomas R Artman
(74) *Attorney, Agent, or Firm* — MLO, a professional corp.

(57) ABSTRACT

An x-ray diffractometer may perform 3D-analysis of collagen tissue of a patient (a human or another animal). The diffractometer includes an oblong housing that may be hinged and that contains an x-ray projector on one side of a recess and a receiver on an opposite side of the recess. The recess accommodates analyzed tissue such as the external ear and skin of a patient. The x-ray projector directs an x-ray micro-beam at the patient's tissue, and the receiver contains a movable two-dimensional x-ray detector that detects a transmitted x-ray micro-beam passed through the analyzed tissue and detects x-rays scattered or diffracted by the analyzed tissue.

18 Claims, 2 Drawing Sheets

(51) Int. Cl.
*A61B 6/08* (2006.01)
*A61B 6/40* (2024.01)
*A61B 6/42* (2024.01)
*A61B 6/50* (2024.01)

(52) U.S. Cl.
CPC .......... *A61B 6/4233* (2013.01); *A61B 6/4405* (2013.01); *A61B 6/4435* (2013.01); *A61B 6/4452* (2013.01); *A61B 6/483* (2013.01); *A61B 6/5205* (2013.01); *A61B 6/08* (2013.01); *A61B 6/4464* (2013.01); *A61B 6/508* (2013.01); *G01N 2223/03* (2013.01); *G01N 2223/054* (2013.01); *G01N 2223/0561* (2013.01); *G01N 2223/1016* (2013.01); *G01N 2223/605* (2013.01); *G01N 2223/6126* (2013.01)

(56) References Cited

U.S. PATENT DOCUMENTS

| | | | |
|---|---|---|---|
| 4,298,797 A | 11/1981 | Bernard et al. | |
| 4,829,549 A * | 5/1989 | Vogel | A61B 6/505 378/146 |
| 5,717,733 A * | 2/1998 | Kurbatov | G01N 23/207 378/71 |
| 5,748,704 A * | 5/1998 | Mazess | A61B 6/482 378/54 |
| 6,175,117 B1 * | 1/2001 | Komardin | A61B 6/483 250/363.06 |
| 6,315,445 B1 * | 11/2001 | Mazess | A61B 6/548 348/E5.088 |
| 6,320,931 B1 * | 11/2001 | Arnold | A61B 6/4233 378/54 |
| 6,405,068 B1 * | 6/2002 | Pfander | A61B 6/482 378/53 |
| 6,718,007 B1 * | 4/2004 | James | A61B 5/448 378/70 |
| 7,136,454 B2 * | 11/2006 | Gerndt | G01N 23/207 378/98.12 |
| 7,794,144 B2 * | 9/2010 | Windt | A61B 6/4035 378/207 |
| 8,553,840 B2 * | 10/2013 | James | A61B 6/483 378/70 |
| 8,971,488 B2 * | 3/2015 | Parham | A61B 6/542 378/85 |
| 9,025,725 B2 * | 5/2015 | Kiyohara | A61B 6/4291 378/197 |
| 9,046,471 B2 * | 6/2015 | Ueji | G06T 11/005 |
| 9,968,314 B1 * | 5/2018 | Sebring | A61B 6/4233 |
| 10,966,677 B2 * | 4/2021 | Matsuura | A61B 6/027 |
| 10,993,685 B2 * | 5/2021 | Schraven | A61B 6/4441 |
| 11,403,793 B2 * | 8/2022 | König | A61B 6/4405 |
| 11,607,188 B2 * | 3/2023 | Lazarev | G16H 50/70 |
| 11,751,828 B2 * | 9/2023 | Lazarev | A61B 6/502 600/408 |
| 12,094,609 B2 * | 9/2024 | Lazarev | G06F 21/602 |
| 12,094,610 B2 * | 9/2024 | Lazarev | G16H 30/20 |
| 2001/0053202 A1 * | 12/2001 | Mazess | H04N 23/81 348/E5.088 |
| 2003/0000291 A1 | 1/2003 | Kolosov et al. | |
| 2003/0012334 A1 | 1/2003 | Kurtz et al. | |
| 2003/0014418 A1 | 1/2003 | Adler et al. | |
| 2005/0259790 A1 * | 11/2005 | Gerndt | G01N 23/207 378/98.12 |
| 2006/0015265 A1 | 1/2006 | Raich | |
| 2007/0032832 A1 | 2/2007 | Feher | |
| 2009/0190722 A1 * | 7/2009 | Windt | A61B 6/06 378/206 |
| 2009/0299642 A1 * | 12/2009 | French | G01N 23/2055 702/19 |
| 2010/0135461 A1 * | 6/2010 | James | A61B 6/48 378/70 |
| 2012/0039438 A1 * | 2/2012 | Parham | A61B 6/4488 378/62 |
| 2012/0091333 A1 * | 4/2012 | French | G01N 33/92 250/282 |
| 2012/0224670 A1 | 9/2012 | Kiyohara et al. | |
| 2013/0077753 A1 * | 3/2013 | James | A61B 6/48 378/71 |
| 2013/0121460 A1 | 5/2013 | Mitsunaga et al. | |
| 2013/0138382 A1 | 5/2013 | Mitsunaga et al. | |
| 2013/0182824 A1 * | 7/2013 | French | G01N 23/20025 378/79 |
| 2013/0259194 A1 * | 10/2013 | Yip | A61B 6/502 378/62 |
| 2013/0259199 A1 * | 10/2013 | Ueji | G01N 23/20008 378/70 |
| 2014/0117247 A1 | 5/2014 | Hamlin | |
| 2015/0030126 A1 | 1/2015 | Radicke | |
| 2015/0233804 A1 | 8/2015 | Meisberger et al. | |
| 2015/0351637 A1 | 12/2015 | Ruppersberg et al. | |
| 2016/0235372 A1 | 8/2016 | Schneider et al. | |
| 2016/0317109 A1 | 11/2016 | Yip et al. | |
| 2017/0160212 A1 | 6/2017 | Kleine et al. | |
| 2017/0362585 A1 | 12/2017 | Wang et al. | |
| 2018/0035961 A1 | 2/2018 | Bartl et al. | |
| 2018/0199901 A1 * | 7/2018 | Schraven | A61B 6/0487 |
| 2019/0115184 A1 | 4/2019 | Zalubovsky | |
| 2019/0154439 A1 | 5/2019 | Binder | |
| 2020/0083080 A1 | 3/2020 | Clark et al. | |
| 2020/0100747 A1 * | 4/2020 | Matsuura | A61B 6/025 |
| 2020/0150061 A1 | 5/2020 | Kriele | |
| 2020/0302660 A1 * | 9/2020 | König | G06T 11/006 |
| 2020/0333265 A1 | 10/2020 | Doki et al. | |
| 2022/0008027 A1 | 1/2022 | Lazarev et al. | |
| 2022/0013227 A1 * | 1/2022 | Lazarev | G16H 40/67 |
| 2022/0013233 A1 * | 1/2022 | Lazarev | G01N 23/201 |
| 2022/0381710 A1 | 12/2022 | Evans | |
| 2022/0415505 A1 * | 12/2022 | Lazarev | G16H 50/20 |
| 2023/0113064 A1 * | 4/2023 | Yuk | G16H 50/20 700/90 |
| 2023/0207074 A1 * | 6/2023 | Lazarev | G06F 21/6245 705/2 |
| 2023/0240635 A1 * | 8/2023 | Lazarev | A61B 6/502 |
| 2023/0240636 A1 * | 8/2023 | Lazarev | A61B 6/5217 600/301 |
| 2023/0270396 A1 * | 8/2023 | Lazarev | G16H 50/20 |
| 2023/0341339 A1 * | 10/2023 | Lazarev | G01N 23/207 |
| 2023/0341340 A1 * | 10/2023 | Lazarev | A61B 6/483 |
| 2024/0000412 A1 * | 1/2024 | Lazarev | G16H 30/20 |
| 2024/0016462 A1 * | 1/2024 | Lazarev | G16H 50/20 |
| 2024/0161893 A1 * | 5/2024 | Lazarev | A61B 5/0075 |

FOREIGN PATENT DOCUMENTS

| | | | | |
|---|---|---|---|---|
| WO | 20210108715 A1 | 6/2021 | | |
| WO | WO-2021257451 A1 * | 12/2021 | .......... | A61B 6/4035 |

OTHER PUBLICATIONS

James, Veronica J., "Fiber diffraction of skin and nails provides an accurate diagnosis of mailgnancies", Int. Journal Cancer: 125, pp. 133-138 (2009).

Kong, Wenyu et al., "Collagen crosslinking: effect on structure, mechanics and fibrosis progression" Biomed. Mater, 16 062005 (2021).

Madhurapantula, Rama Sashank et al., "X-ray Diffraction D-Periodic Location of Native Collagen Crosslinks In Situ and Those Resulting from Non-Enzymatic Glycation," Accelerator Physics—Radiation Safety and Applications, Chapter 7, pp. 149-168 (2018) http://dx.doi.org/10.5772/intechopen.71022.

Fagundes et al., "Structural characterization of canine mammary tissue by x-ray diffraction", Radiation Physics and Chemistry, vol. 155, pp. 22-25. (Year: 2019).

Ghammraoui et al., "Maximum-likelihood estimation of scatter components algorithm for x-ray coherent scatter computed tomography of the breast", Physics in Medicine & Biology, vol. 61, pp. 3164-3179. (Year: 2016).

(56) References Cited

OTHER PUBLICATIONS

Graewet et al., "Impact and progress in small and wide angle X-ray scattering (SAXS and WAXS)", Current Opinion in Structural Biology, vol. 23, pp. 748-754. (Year: 2013).
Office Action dated Nov. 5, 2024 for U.S. Appl. No. 18/137,356.
Translation of CN 110907483 A (Year: 2019).
Translation of CN-109324072-B (Year: 2021).

* cited by examiner

DIFFRACTIVE ANALYZER OF PATIENT TISSUE

REFERENCE TO RELATED APPLICATIONS

This patent document claims benefit of the earlier filing date of U.S. provisional Pat. App. No. 63/333,079, filed Apr. 20, 2022, which is hereby incorporated by reference in its entirety.

BACKGROUND

Early diagnosis of a malignancy directly correlates with successful treatment of the malignancy. Unfortunately, no noninvasive, cost-effective diagnostic tests are readily available for many malignancies, which results in patients often presenting too late for effective treatment.

Fiber diffraction patterns of skin or fingernails, using x-ray sources, has been proposed as a biometric diagnostic method for detecting neoplastic disorders including but not limited to melanoma and breast, colon, and prostate cancers. Veronica J. James, "Fiber diffraction of skin and nails provides an accurate diagnosis of malignancies", Int. J. Cancer: 125, 133-138 (2009), suggests that with further development, procedures using small angle x-ray beam lines at synchrotrons may provide a confirmatory or diagnostic tests that could be conducted on a regular basis in local radiology facilities. In such tests, samples of human and animal hair, nails, and skin could be used for "indirect" detection and diagnosis of various diseases.

The effect of different endogenous and exogenous factors on the molecular and nano structural ordering of human hair has been studied using x-ray fluorescence and diffraction from synchrotron radiation. The diffraction hair causes may be attributed to two fibrillar systems of tissue: the intermediate keratin filaments of the cytoskeleton of the hair and the proteoglycan fibrils of the extracellular matrix of the hair. The effect that personal hygiene products and medicines have on the structural transformation and elemental composition of hair may be investigated. Proteoglycans are considered as universal components of a matrix that ensure the structural homeostasis of biological tissue subjected to endogenous and exogenous effects. Hair may be a promising biological material for solving applied problems when used as a diagnostic material for the widescale monitoring of environmental and public health risks.

Mark R. Goldstein, Luca Mascitelli, "Might tumor secreted cathepsin proteases leave specific molecular signals in skin, hair and nails years before a cancer becomes clinically apparent?", Medical Hypotheses 103 (2017) 62-63, suggests that X-ray fiber diffraction analysis (FDA) of the fibrous macromolecules in hair, nails and skin may allow diagnosis of various cancers, at sites remote from the cancer and years before the cancer becomes clinically apparent. Currently, this technology is not widely accepted because of reproducibility issues and a lack of an explanation as to how a clinically unapparent tumor can leave molecular "signatures" at remote sites. However, some evidence suggests that tumor-specific cathepsins (lysosomal proteases) circulate systemically long before a cancer is clinically apparent. One possible mechanism that could leave a signature for FDA is that cathepsins, by virtue of their proteolytic activity, impart molecular changes in tissues remote from the primary tumor. FDA of hair, nails, and skin might detect these subtle molecular changes, which may be specific for various tumors.

Some publications have indicated that the structure of collagen changes in patients (animals and humans) suffering from severe oncological diseases.

Synchrotron based x-ray diffraction experiments may also be effective in the study of mammalian connective tissues and related diseases. Rama Sashank Madhurapantula and Joseph P. R. O. Orgel, "X-Ray Diffraction Detects D-Periodic Location of Native Collagen Crosslinks In Situ and Those Resulting from Non-Enzymatic Glycation", http://dx.doi.org/10.5772/intechopen.71022 describe observing changes in the structure of Extra-Cellular Matrix (ECM), induced in an ex-vivo tissue based on a model of the disease process underlying diabetes. Pathological changes to the structure and organization of the fibrillar collagens within the ECM, such as the formation of nonenzymatic crosslinks in diabetes and normal aging, have been shown to play an important role in the progression of such maladies. However, without direct, quantified, and specific knowledge of where in the molecular packing these changes occur, development of therapeutic interventions has been impeded. In vivo, the result of non-enzymatic glycosylation e.g., glycation, is the formation of sugar-mediated crosslinks, aka advanced glycation end-products (AGEs), within the native D-periodic structure of type I collagen. The locations for the formation of these crosslinks have been inferred from indirect or comparatively low-resolution data under conditions likely to induce experimental artifacts. Sashank et al. indicate x-ray diffraction derived data, collected from whole hydrated and intact isomorphically derived tendons, that indicate the location of both native (existing) and AGE crosslinks in situ of D-periodic fibrillar collagen.

Biophysical properties of an extracellular matrix (ECM), such as matrix stiffness, viscoelasticity, and matrix fibrous structure, are emerging as important factors that regulate progression of fibrosis and other chronic diseases. See Wenyu Kong et al, "Collagen crosslinking: effect on structure, mechanics and fibrosis progression", 2021 Biomedical Materials 16 062005. The biophysical properties of the ECM can be rapidly and profoundly regulated by crosslinking reactions in enzymatic or non-enzymatic manners, which further alter the cellular responses and drive disease progression. In-depth understandings of crosslinking reactions may help reveal the underlying mechanisms of fibrosis progression and put forward new therapeutic targets, whereas related reviews are still devoid. Kong et al. focus on the main crosslinking mechanisms that commonly exist in many chronic diseases (e.g., fibrosis, cancer, osteoarthritis) and summarize current understandings including the biochemical reaction, the effect on ECM properties, the influence on cellular behaviors, and related studies in disease model establishment.

DETAILED DESCRIPTION

A diffractometer in accordance with one example disclosed herein may be used to study the phase composition of collagen tissue and disturbances of periodic structure in collagen tissue. The phase composition and disturbances, which illness may cause, may be identified to develop diagnostic criteria based on diffractometer measurement data. The diffractometer may be particularly adapted to analyze a patient's external ear and skin, which generally contains multiple types of collagen, e.g., collagen I and collagen II.

An x-ray system in accordance with another example of the present disclosure may provide x-ray 3D-analysis of an external ear and skin collagen tissue of a human or other animal. The x-ray system may be used to detect matrix related diseases, including, but not limited to, inflammation, melanoma, breast, colon, and prostate cancer and used to the study of changes in tissue structure of these foci. The x-ray system may be suitable for human and veterinary medicine and may provide easily accessible, non-invasive, cost-effective diagnostic tests at early stages of diseases.

A diffractometer in accordance with another example of the present disclosure may provide x-ray 3D-analysis of external ear and skin collagen tissue of a patient, i.e., a human or other animal. A specific example of a diffractometer may include: an oblong housing defining a recess where the external ear and skin of a patient may be placed. X-ray devices may be located in the housing on opposite sides of the recess. One x-ray device in the diffractometer may be an x-ray projector that produces and directs a primary incident micro-beam of x-rays at analyzed tissue, e.g., the external ear and skin of a patient, and another x-ray device may be a receiver system including a movable two-dimensional pixel detector capable of detecting the transmitted micro-beam of x-rays passed through the analyzed tissue and detecting some or all x-rays that the analyzed tissue diffracts from the incident micro-beam beam.

X-ray systems or diffractometers in accordance with some examples disclosed herein may provide 3D analysis of the molecular or nano-scale structure of living tissue, particularly of the external ear and skin of a human or other animal patient and more particularly of collagen tissue in the external ear or skin of the patient.

Figure 1:
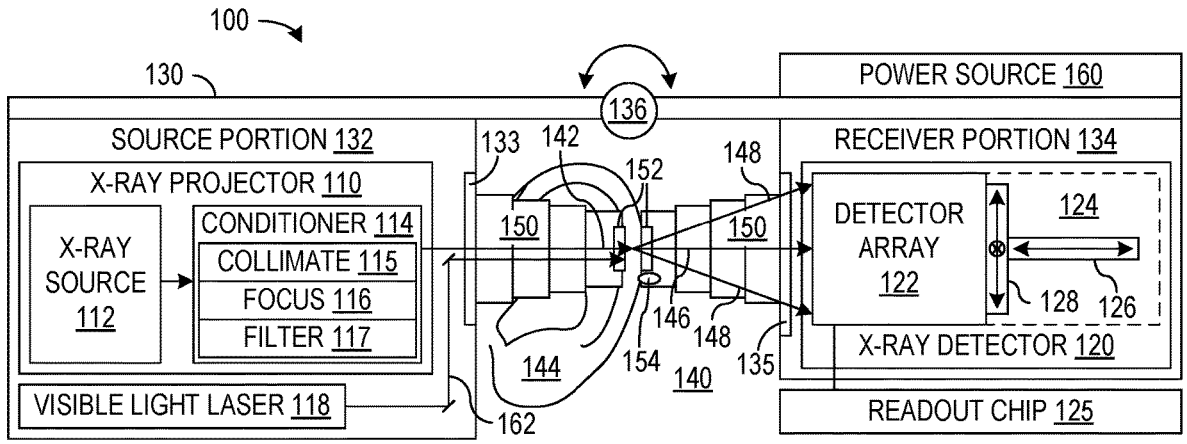
FIG. 1 is a block diagram illustrating an example of an x-ray diffractometer in accordance with an example of the present disclosure.

FIG. 1 shows a block diagram of a diffractometer 100 in accordance with an example of the present disclosure. Diffractometer 100 includes an x-ray projector 110 and an x-ray detector 120. X-ray projector 110 directs an x-ray beam 142 into a tissue holding area 140, and x-ray detector 120 is positioned to detect an x-ray scattering or diffraction pattern resulting when x-ray beam 142 from x-beam projector 110 interact with tissue of a patient, e.g., an external ear or skin 144 of a human or other animal being examined.

X-ray projector 110 in the illustrated example includes an x-ray source 112 and an x-ray beam shaper or conditioner 114. X-ray source 112 may include, for example, an x-ray tube or x-ray laser. X-ray beam conditioner 114 may include one or more collimating systems 115, focusing systems 116, or filter systems 117. For example, collimating systems 115 may include a Kratki or Montel mirror collimator. Focusing systems 116 may include grazing-incidence mirrors that are slightly curved to focus x-ray beam 142. Filter systems 117 of x-ray beam conditioner/shaper 114 may include, for example, at least one monochromator. In one specific example, x-ray source 112 includes a radiation source operating in continuous mode, e.g., x-ray tube, to produce monochromatic x-rays and x-ray beam conditioner 114 includes a collimating mirror and aperture that form or shape the x-ray micro-beam 112. Alternatively, x-ray beam conditioner 114 may employ any other systems capable of controlling the width, collimation, or other characteristics of x-ray beam 142.

In operation, beam conditioner 114 receives x-rays from x-ray source 112 and produces an x-ray beam 142 having desired intensity, wavelength, and beam profile. X-ray beam 142 may, for example, be is a micro-beam having a FWHM of about 200 microns or less, a wavelength of 1.60 Å to 0.3 Å, and an intensity on the order of about 1012 photons/sec/mm$^2$.

X-ray beam 142 from x-ray beam projector 110 passes into area 140 where patient tissue such as an external ear or skin 144 of the patient (human or other animal) may be presented. X-ray beam 142 enters and interacts with external ear or skin 144, where x-rays scatter or diffract. As a result, both transmitted, i.e., unscattered, x-rays 146 and scattered x-rays 148 enter x-ray detector 120.

X-ray detector 120 in the illustrated example includes a detector array 122 or other system capable of detecting a distribution of x-rays. Detector array 122 may be a two-dimensional array of pixel sensors, with each pixel sensor being a photodiode or transistor that is sensitive to x-rays. Detector array 122 is mounted on a detector mounting system or stage 124 that is operable to move detector array. In the illustrated example, detector mounting system 124 includes an actuator or detector position adjuster 126 capable of mechanically moving pixel detector 122 toward or away from tissue holding area 140 along the propagation direction of incident x-ray beam 142 and transmitted x-ray beam 146. Detector position adjuster 124 may, for example, include a drive train 126 of a type used to adjust the height of optics assemblies in photocopiers.

Movement of pixel detector array 122 relative toward or away from the analyzed tissue, e.g., the external ear and skin 144 of the patient, can change the measurement resolution and the measurement range of radiation 148 that the analyzed tissue scatters. For instance, moving detector array 122 further from the analyzed tissue increases the area of detector array 122 exposed to radiation 148 scattered over small angles and thereby improves the ability of x-ray detector 120 and array 122 to resolve a small angle scattering pattern. On the other hand, moving detector array 122 closer to the analyzed tissue 144 enables radiation 148 that the analyzed tissue 144 scatters or diffracts to larger angles to strike detector array 122, allowing x-ray detector 120 and array 122 to measure radiation 148 scattered at larger angles, e.g., close to 90° if detector is sufficiently close to analyzed tissue 144. Diffractometer 100 may thus position detector array 122 to measure x-ray scattering at a desired resolution or in a desired range of angles. For examples, movement along the beam direction can position detector array 122 for high resolution diffraction measurements over a small range of angles (e.g., angles less than 1°) or for diffraction measurements over a large range of angles (e.g., angles approaching 90°).

Pixels in detector array 122 generally need to be sensitive enough to detect or measure scattered x-rays, which are generally much less intense than transmitted x-rays 146. To extend the operational life of detector array 122, detector mount 124 for detector array 122 may further include a mechanism 128 that excites transverse vibrations of detector array 122. The vibrations move detector array 122 so that transmitted x-rays 146 are not constantly striking the same pixel or pixels in detector array, but instead, strike different pixels at different times. By exciting vibrations of detector array 122 that are transverse relative to transmitted x-ray beam 146 and larger in amplitude than the width of transmitted x-ray beam 146, mechanism 128 may prevent the high intensity of transmitted x-ray beam 146 from quickly burning out the central pixel or pixels, i.e., the pixels of detector array 122 that measure the transmitted x-ray beam 146 and identify the center of an x-ray diffraction pattern. X-ray diffraction pattern measurements, e.g., frames captured by detector array 122, at different times during a transverse vibration of detector array 122 can be electronically or digitally centered and combined or calibrated to account for the difference in the transverse position detector array 122.

Different examples of diffractometer 100 may use different types of transverse vibrations of detector array 122. In one example disclosed herein, diffractometer 100 drives mechanism to excite a longitudinal surface acoustic wave causing transverse vibrations of detector array 122. The vibrations may include linear fluctuations only in the equatorial direction (e.g., perpendicular to the page of FIG. 1), linear fluctuations only in the meridional direction (e.g., vertical in FIG. 1), or two-dimensional fluctuations in the equatorial and meridional directions simultaneously.

Mechanism 128 in one example contains piezoelectric actuators and uses the piezoelectric effect to drive the transverse vibration or oscillations of detector array 122. The amplitude of the transverse vibrations of detector array 122 may be at least as large as the pitch of pixels in detector array 122 or the FWHM width of transmitted beam 146. In still another aspect disclosed herein, the frequency of the transverse vibrations of detector array 122 may be less than or equal to a frame rate at which the two-dimensional pixel detector acquired measurements. In general, the frequency of oscillations may be several, e.g., 4 to 6, orders of magnitude less than the frequency of frame capture. A readout chip 125 for detector array 122 can control the speed and timing of transverse movements of detector array 122 or a frame rate at which detector array 122 captures measurements to avoid smearing of the x-ray pattern measurements that detector array 122 captures in respective frames.

In yet another aspect disclosed herein, readout chip 125 implements a known operating mode, sometimes referred to as Charge Summing Mode (CSM), with the purpose of eliminating charge-shared events. More particularly, x-ray photons striking pixel sensors in an array may cause charge accumulation or other effects on neighboring pixels. In one case, readout chip 124 can sum signals from neighboring pixels at a series of "summing nodes" and assign each hit to the node or pixel with the highest signal, to thereby compensate for charge-sharing and similar effects.

In accordance with another aspect of the present disclosure, diffractometer 100 does not employ a beam stop. Avoiding use of a beam stop near detector array 122 and particularly avoiding need of a beam stop in front of detector array 122 avoids parasitic scattering or backscattering of x-rays from the beam stop and may reduce noise and provide more accurate measurement or detection of scattering of x-ray micro-beam 142 of x-rays from analyzed tissue 144.

In another aspect disclosed herein, diffractometer 100 may include an oblong housing 130 that is hinged. In the example of FIG. 1, housing 130 includes a source portion 132, a receiver portion 134, and a swivel joint or hinge 136 that connects source portion 132 to receiver portion 134 and allows folding of housing 130, e.g., for transportation of diffractometer 100. Source portion 132 of housing 130 may contain or provide a mounting for x-ray beam projector 110 on one side of hinge 136, and receiver portion 134 may attach to or contain mounting 124 for detector array 122 on the other side of hinge 136. Interiors of source portion 132 and receiver portion 134 may be at a vacuum pressure or filled with an inert gas, e.g., neon or helium, and source portion 132 or receiver portion 134 may have a wall or window 133 and 135 that faces tissue holding area 140 and that is transparent to x-rays. In particular, x-ray projector 110 may be sealed in source portion 134 (or a protection container) that is vacuumed or filled with an inert gas, and detector array 122 may similarly be in receiver portion 134 or another protection container that is vacuumed or filled with an inert gas.

In still another example disclosed herein, one or more of x-ray beam projector 110, source portion 132, and receiver portion 134 may be equipped with telescoping structures 150 that can extend to (and retract from) contact with the surface of analyzed tissue 144 to hold or fix analyzed tissue 144 during x-ray diffraction analysis. Each telescoping structure 150 may surround the optical paths of incident x-ray beam 142 or transmitted x-rays 146 and scattered x-rays 148 and may contain a vacuum or an inert gas to reduce any scattering or attenuation of scattered x-rays 148 between analyzed tissue 144 and detector array 122.

In yet another example disclosed herein, each telescoping structure 150 may be equipped with a window 152, e.g., a beryllium window, that is transparent to x-rays. Windows 152 may seal off the vacuum areas inside telescoping structures 150 from the non-vacuum area 140 for patient tissue 144. In yet another example, telescoping structures 150 further include a contact pressure sensor 154 that senses a force or compression that extension of the telescoping structures 150 applies to the external ear and skin or other patient tissue 144 so that a control system of diffractometer 100 can regulate the force that telescoping structures 150 apply to the patient.

In yet another example, diffractometer 100 may further include a visible light laser 118. Visible light laser 118 may be aligned with or part of x-ray beam projector 110, so that a visible beam 162 from laser 118 may be used to place a visible spot on analyzed patient tissue 144 for pointing of the diffractometric x-ray beam 142 at a selected point on analyzed tissue 144.

In another example, a mobile version of diffractometer 100 has a small size, e.g., less than about 1.5 m in length when fully extended. The mobile version of diffractometer 100 may employ hinge 136 to fold diffractometer 100 so that source portion 132 and receiver portion 134 are adjacent to each other and the length of diffractometer 100 is shortened bay about one half, e.g., less than 75 cm. The mobile version of diffractometer 100 may be equipped with an autonomous power source 160, which may be based on electric accumulators or batteries. In another example, diffractometer 100 is designed to be installed on vehicle such as an automobile, and power source 160 for diffractometer 100 is an automotive electric generator, battery, or other automotive electrical system.

Figure 2:
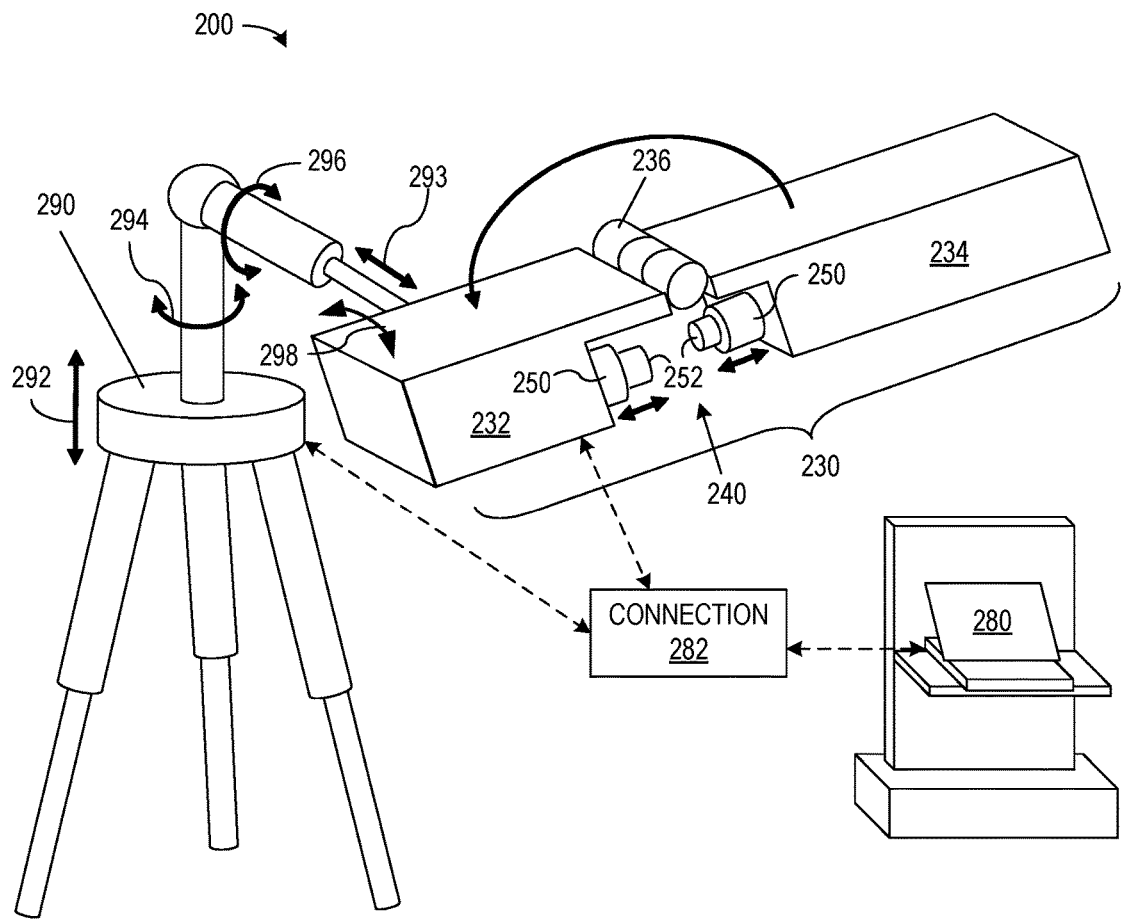
FIG. 2 schematically shows a perspective view of an x-ray diffractometer system according to an example of the present disclosure.
Figure 3:
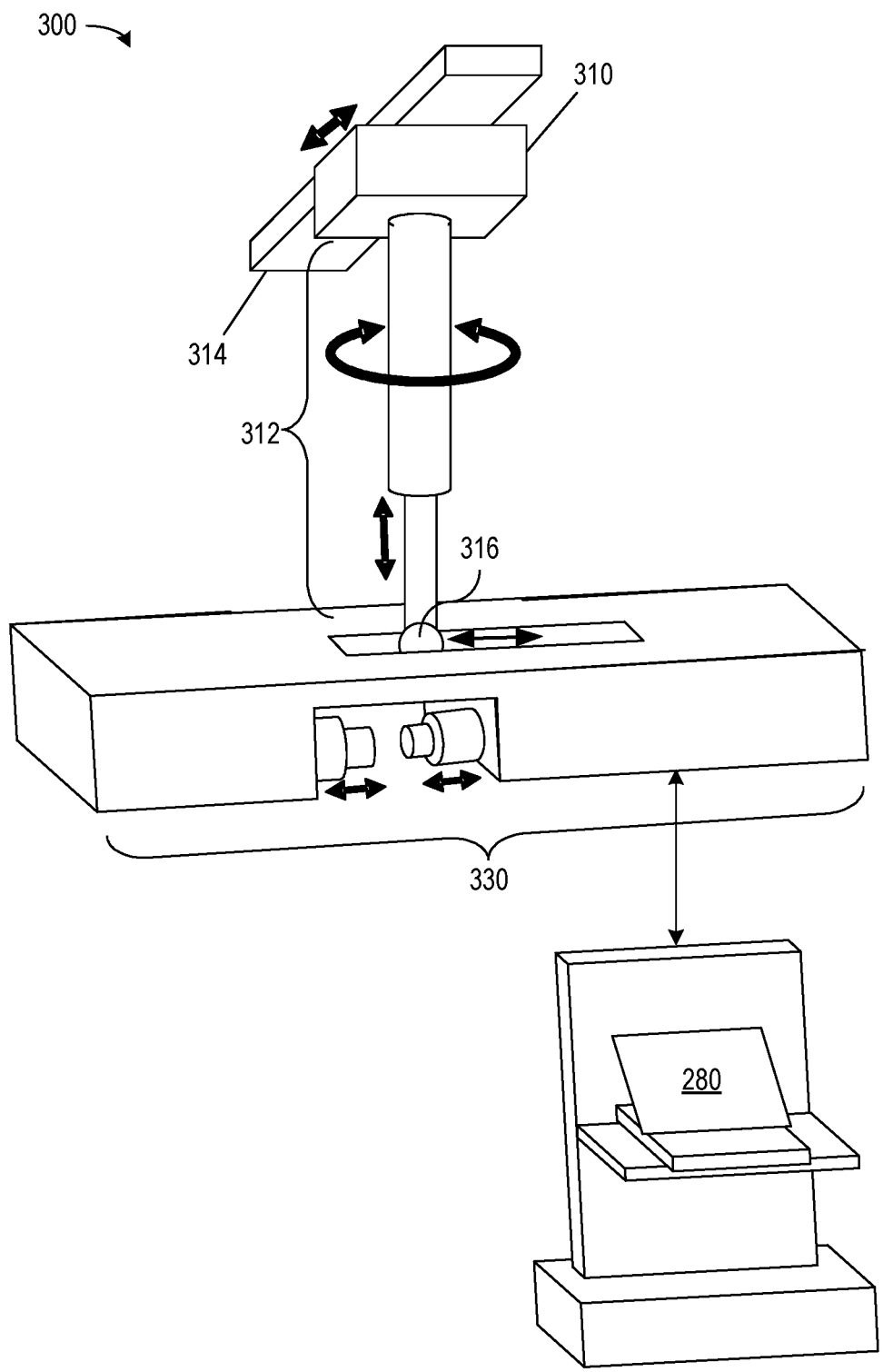
FIG. 3 schematically shows the perspective view of an x-ray diffractometer system according to another example of the present disclosure.

FIGS. 2 and 3 are schematic representations of examples of alternative diffractometer systems in accordance with specific examples, and elements illustrated in the drawings are not necessarily shown to scale. Rather, the various elements are represented in FIGS. 2 and 3 to illustrate the functions and general purposes of the elements. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

FIG. 2 schematically shows a perspective view of an x-ray diffractometer system 200 for x-ray 3D-analysis of collagen tissue such as the external ear and skin of a patient (not shown). Diffractometer system 200 includes a diffractometer 230 having an x-ray source portion 232, an x-ray receiver portion 234, and a hinge or swivel joint 236 connecting x-ray source portion 232 and x-ray receiver portion 234. Source portion 232 and receiver portion 234 are shaped and connected (via joint 236) to define a recess 240 that may surround the external ear or other tissue of a patient being examined. X-ray source portion 232 contains a source of an x-ray beam that directs an x-ray micro-beam into recess 240, and swivel joint 236 may be used to position a detector in x-ray receiver portion 234 to receive and measure x-rays that are transmitted through or scattered by the patient's tissue. For example, swivel joint 236 may position x-ray receiver portion 234 straight across from x-ray source portion 232, so that a center point of a detector in x-ray receiver portion 234 is aligned with the x-ray beam from x-ray source portion 232. Swivel joint 236 further permits folding of x-ray source portion 232 and x-ray receiver portion 234 into a more compact configuration, e.g., for transportation.

X-ray source portion 232 and x-ray receiver portion 234 may be equipped with telescoping structures 250 that may be retracted at the beginning of an x-ray diffraction examination process and then extended to fix a patient's external ear and skin in place for the x-ray diffraction examination. X-ray source portion 232 and x-ray receiver portion 234 may include separate containers, each holding a vacuum around the x-ray source or receiver components, and one or more sealed beryllium walls or windows 252 may be located at one or both ends of each telescoping structure 250. X-ray receiver portion 234 may contain a movable two-dimensional pixel detector designed to detect the transmitted micro-beam of x-ray passed through the analyzed tissue as well as detect part or all x-rays that are diffracted or otherwise scattered by the analyzed tissue. X-ray receiver portion 234 may further include a mechanism for moving the movable two-dimensional pixel detector along the direction of the incident micro-beam of x-ray, and the two-dimensional pixel detector may provide approximately the same relative resolution of diffraction measurements at small angles (less than about 1°) and large angles (up to about 90°). The mechanisms moving the sliding two-dimensional detector, by way of example and not by way of limitation, may employ a ball-screw motion transmission, which transmits the rotational movement from an electrical motor to the translational movement of the two-dimension detector. X-ray receiver portion 234 may also include one or more devices designed for excitation of vibrations of the two-dimensional pixel detector that are transverse relative to the incident x-ray beam. In general, the mechanism providing transverse movement or vibration of the detector array may operate independently of the mechanism that moves the detector array along the beam direction.

Diffractometer 230 attaches to a mounting structure such as a tripod 290 with collapsible (demountable) connecting device, and tripod 290 may include motorized or manual mechanism that permit positioning and orienting diffractometer 230 to accommodate a location on a patient of the tissue to be examined. Such movement systems may include adjustment systems 292 and 293 for the height and separation of the diffractometer 230 from the base of tripod 290 and adjustment systems 294, 296, and 298 for control of the yaw, pitch, and roll of diffractometer 230.

A computer workstation 280, which may be a conventional general-purpose computer with hardware such as one or more microprocess with associated memory and I/O interfaces, may execute software or firmware to control drive systems of tripod 290 to control the position and orientation of diffractometer 230. Computer workstation 280 may also receive and process measurement from diffractometer 230, conduct diffractometric structural analysis using the measurements received, processes or identify one or more diffraction patterns that the structural analysis found, and store and display the obtained data. Computer workstation 280 may exchange data and control signals with diffractometer 230 or tripod 290 over a connection 282, which may, for example, be a wired or wireless communication channel or network device.

Computer workstation 280 in some diffractometer systems may be configured and connected to control one or multiple x-ray devices, e.g., x-ray sources and detectors, control drive mechanisms and motors, e.g., for detector position or orientation adjustment, and may acquire, store, and process measurement data from multiple x-ray detectors. Computer workstation 280 may process, store and display data or results from the 3-D diffractometric structural analysis, e.g., from calculation of parameters of the three-dimensional reciprocal lattice of the studied collagen tissue.

FIG. 3 shows an example of an x-ray diffractometer system 300 including an x-ray diffractometer 330 held in a wall or a ceiling mount 310, which may be installed in a laboratory or examination room. Other than its mounting structure, diffractometer 330 may be substantially identical to diffractometer 200 of FIG. 2, and diffractometer system 300 may contain the same or similar components to those described above with reference to FIG. 2. Wall or ceiling mount 310 includes a telescoping arm 310 extending between a wall or ceiling mounting structure 314 and a ball joint connection structure 316 for diffractometer 330. Mount 310 may allow independent movement of arm 312 along an actuation direction of wall or ceiling mounting 314, rotation of arm 312 about a length axis of arm 312, extension and retraction of the length of arm 312, and pitch, roll, and yaw rotations of diffractometer on ball joint 316 for control of the position and orientation of diffractometer 330 in three dimensions. Mount 310 may further include mechanisms and motors designed to move telescoping arm 312 and mounting structures 314 and 316 along their respective degrees of freedom of motion. In yet another aspect disclosed herein, movement of diffractometer 330 may be realized by using appropriate mechanisms such as a ball-screw motion transmission or a combination of a feed screw shaft that is driven to rotate by a position-controllable electric motor and a slide member that is held in thread-engagement with the feed screw shaft as well as using a step motor. In another example, a rotation of diffractometer 330 may be realized by using appropriate rotary drive mechanisms such as a tangent bar type drive mechanism where the drive source is preferably a position-controllable electric motor such as a pulse motor or a servomotor.

Although aspects of the present disclosure have been described in detail with reference to certain implementations or examples, persons possessing ordinary skill in the art to which this disclosure pertains will appreciate that various modifications and enhancements may be made without departing from the spirit and scope of the claims that follow. Any feature, whether preferred or not may be combined with any other feature whether preferred or not. Alternatives to the examples described herein can be employed in practicing the invention as defined in the following claims. It is intended that the following claims define the scope of the invention and that methods and structures within the scope of these claims and their equivalents be covered thereby. The appended claims are not to be interpreted as including means-plus-function limitations, unless such a limitation is explicitly recited in a given claim using the phrase "means for."

What is claimed is:

1. A diffractometer system comprising:
    a housing including a source portion and a receiver portion with a recess between the source portion and the receiver portion, the recess accommodating patient tissue to be analyzed;
    an x-ray projector in the source portion and projecting an x-ray beam into the recess;
    an x-ray receiver in the receiver portion, the x-ray receiver including an array of x-ray sensors positioned to detect x-rays from the x-ray beam that are transmitted undeflected through the recess and x-rays from the x-ray beam that the patient tissue in the recess scatters; and
    one or more telescoping structures on at least one of the source portion and the receiver portion, each of the telescoping structures extending to and fixing the patient tissue in place during an x-ray examination process.

2. The diffractometer system of claim 1, further comprising a computer system connected to the x-ray projector and the x-ray receiver, wherein the computer system is configured to control the x-ray projector and the x-ray receiver, process, store, and display data received from the x-ray receiver, perform 3-D diffractometric structural analysis, and calculate parameters of a three-dimensional reciprocal lattice of collagen in the patient tissue.

3. The diffractometer system of claim 1, wherein the x-ray projector comprises a radiation source and a beam conditioner forming the x-ray beam, the radiation source operating in continuous mode, and the beam conditioner including at least one monochromator, an x-ray collimating device, and an x-ray focusing device.

4. The diffractometer system of claim 1, wherein the patient tissue includes an external ear of a patient, and each of the telescoping structures presses against a skin surface of the external ear to hold the patient tissue in place for the x-ray examination process.

5. The diffractometer system of claim 4, where at least one of the telescoping structures further comprise a pressure sensor, the pressure sensor measuring force or compression applied to the external ear.

6. The diffractometer system of claim 1, wherein the source portion and the receiver portion are sealed to hold a vacuum or an inert gas and are equipped with beryllium windows through which the x-ray projector projects the x-ray beam and the x-ray receiver receives the x-rays.

7. The diffractometer system of claim 1, wherein the array of x-ray sensors is in a protection container that is vacuumed or filled with an inert gas.

8. The diffractometer system of claim 1, wherein the housing further comprises a swivel joint that connects the source portion to receiver portion and permits rotation of the receiver portion relative to the source portion.

9. The diffractometer system of claim 1, wherein the receiver portion further comprises:
    a first mechanism connected to move the array of x-ray sensors in a first direction toward or away from the recess; and
    a second mechanism coupled to excite vibrations of the array of x-ray sensors in a second direction that is transverse to the first direction.

10. The diffractometer system of claim 9, where the second mechanism is coupled to excite one or more types of transverse vibrations selected from a group consisting of fluctuations only in an equatorial direction perpendicular to the first direction, fluctuations in a meridional direction perpendicular to the first direction and to the equatorial direction, and fluctuations in both the equatorial and meridional directions simultaneously.

11. The diffractometer system of claim 1, wherein the x-ray projector comprises a radiation source selected from a group consisting of an x-ray tube and an x-ray laser.

12. The diffractometer system of claim 1, further comprising a tripod coupled to the housing, the tripod including a motorized positioning mechanism coupled to move and orient the housing.

13. The diffractometer system of claim 12, wherein the motorized positioning mechanism comprises at least one of a ball-screw motion transmission and a combination of a feed screw shaft that is driven to rotate by a position-controllable electric motor and a slide member that is held in thread-engagement with the feed screw shaft as well as using a step motor.

14. The diffractometer system of claim 1, wherein the x-ray projector further comprises a Kratki or Montel mirror collimator.

15. The diffractometer system of claim 1, further comprising a visible-light laser providing a light beam that is parallel to the x-ray beam in the recess.

16. The diffractometer system of claim 1, further comprising an autonomous power source based on electric accumulators and batteries.

17. The diffractometer system of claim 16, wherein the autonomous power source is an automotive electrical system.

18. The diffractometer system of claim 1, further comprising:
    a telescoping arm attached to the housing and to a wall or a ceiling of a room; and
    mechanisms and motors coupled to move the telescoping arm.

* * * * *